(12) United States Patent
Kankkunen et al.

(10) Patent No.: US 6,394,087 B1
(45) Date of Patent: May 28, 2002

(54) ARRANGEMENT IN ANESTHESIA APPARATUS

(75) Inventors: Jukka Kankkunen, Vantaa; Antti Särelä, Espoo; Tom Häggblom, Vantaa; Teuvo Reinikainen, Espoo, all of (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/154,304

(22) Filed: Sep. 16, 1998

(30) Foreign Application Priority Data

Sep. 24, 1997 (FI) .................................................. 973769

(51) Int. Cl.[7] ............................................. A61M 15/00
(52) U.S. Cl. ............................. 128/203.16; 128/203.12
(58) Field of Search ....................... 128/200.14, 200.23, 128/203.12, 203.13, 203.16, 205.24

(56) References Cited

U.S. PATENT DOCUMENTS

| 4,867,212 A | * | 9/1989 | Mohr et al. ............ 128/203.12 |
| 5,505,236 A | * | 4/1996 | Grabenkort et al. ... 128/203.12 |
| 5,617,906 A | | 4/1997 | Braatz et al. |

FOREIGN PATENT DOCUMENTS

| EP | 781570 | 7/1997 |
| EP | 4781571 | 7/1997 |
| WO | 96/06301 | 2/1996 |

* cited by examiner

*Primary Examiner*—Glenn K. Dawson
(74) *Attorney, Agent, or Firm*—Andrus, Sceales, Starke & Sawall, LLP

(57) ABSTRACT

An arrangement in an anesthesia apparatus, the anesthesia apparatus comprising a filling device located by a vaporizer and an anesthetic bottle that fits the filling device, the filling device being provided with a valve device, which is arranged to open and close as needed. To provide a controlled discharging of anesthetic, the arrangement comprises a discharge space, which is connected to an interspace formed between the anesthetic bottle and the valve device located in the filling device when the anesthetic bottle is being pulled outward, and a closing member, which, as a result of the anesthetic bottle being pulled outward, is arranged to open a flow connection between the interspace and the discharge space before the connection between the anesthetic bottle and the filling device opens.

14 Claims, 3 Drawing Sheets

ARRANGEMENT IN ANESTHESIA APPARATUS

Figure 1:
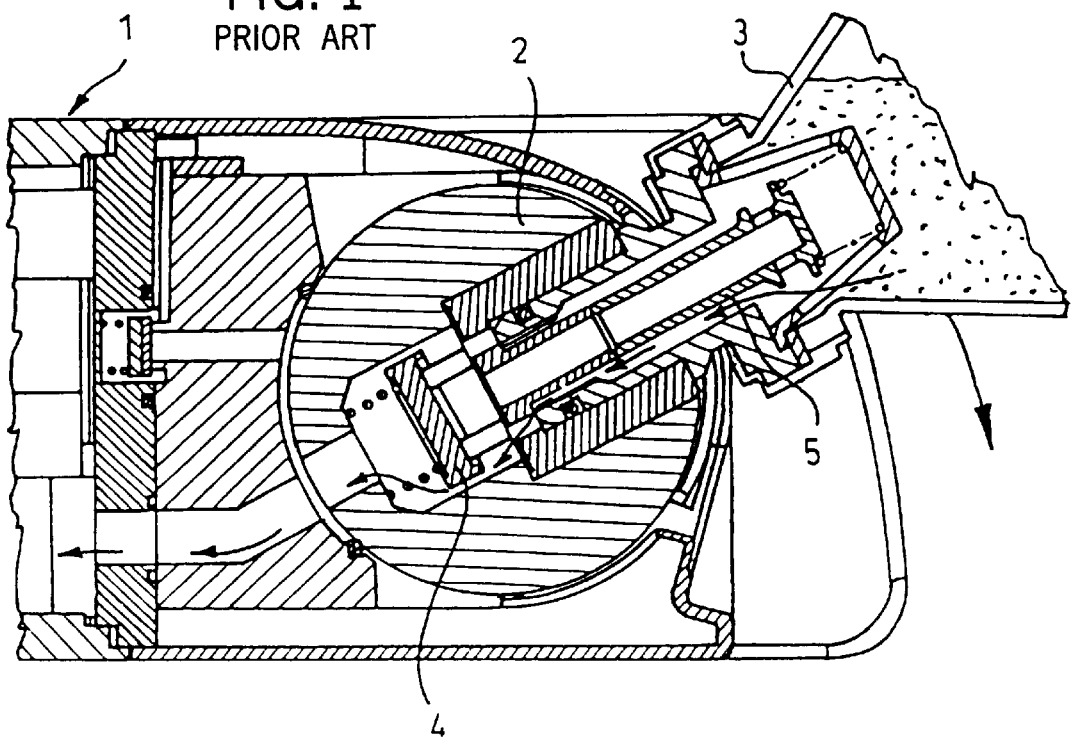

The invention relates to an arrangement in an anesthesia apparatus, the anesthesia apparatus comprising a vaporizer and a dosing device for anesthetic and the arrangement comprising a filling device in connection with the vaporizer and an anesthetic bottle that fits the filling device, the filling device being provided with a valve device, which is arranged to open and close as needed.

Anesthesia apparatuses are used during surgery in operating theaters in hospitals. The most essential components of an anesthesia apparatus are a vaporizer and a dosing device for anesthetic. The components can be integrated or separate units, as in cassette-type structures. The main components of a vaporizer are a liquid container including a vapor generator, and a filling device. The filling device serves to supply the anesthetic to or remove it from the liquid container. Anesthetic agents, i.e. anesthetic liquids, are stored in dispensing cylinders, such as transport and storage containers, also referred to as bottles. Each anesthetic has a dedicated, profile-coded bottle opening, so a storage bottle can only be connected to a filling device suitable for a respective anesthetic, either directly or through a profile-coded adapter.

There are various anesthetic liquids, of which desflurane can be mentioned here. A special characteristic of desflurane in comparison with other anesthetic liquids is that desflurane boils at room temperature, whereby the pressure inside the bottle rises as the temperature rises. For this reasons the opening of a desflurane anesthetic bottle is provided with a profile-coded valve device, the normal position of which is a "closed" position. In addition to the bottle and the valve, the structure also comprises a closing lid, which is screwed on top of the valve to ensure the prevention of leakage during a longer period of storage.

The valve construction of a desflurane bottle is of such type that the bottle seals with the filling part of the vaporizer on the outer edge of the valve and the valve is activated to open and close from the bottom of the inner recess of the front surface. Due to the construction, there is an interspace between the valve seal and the filling part of the vaporizer where is always left a small amount of anesthetic and gaseous anesthetic, which are released in the ambient atmosphere towards the end of the filling situation at a pressure determined for instance by temperature differences of the bottle and the filling device. It is particularly important that the capacity of the above mentioned interspace is as small as possible to ensure that the amount of hazardous spatters of anesthetic sprinkled in the surroundings or, in the worst case, on the operator's hands and in his/her face remains small.

In an attempt to minimize the amount of anesthetic remaining in said interspace, in prior art arrangements the tilt angle of the bottle has been set at 45° from a horizontal level. The tilt angle can be used to influence the flow rate of the anesthetic and the amount of waste anesthetic, the amount of anesthetic remaining in the interspace being determined by the top threshold of the bottle opening and the tilt angle. The flow rate must also be sufficiently high so as to allow a maximum amount of anesthetic to flow during a rapid emptying operation. On the other hand, a large tilt angle can be harmful since a disadvantageous angle causes waste anesthetic to be spattered on the operator's hands. It is thus possible to mathematically calculate the tilt angle that will minimize the amount of waste anesthetic, but an optimal tilt angle consists of various factors.

A problem in prior art solutions has been that they have not provided for a controlled management of the amount of waste anesthetic and gaseous anesthetic remaining in the interspace to ensure that it does not provide a risk to the operator.

An object of the invention is to provide an arrangement that will allow the drawbacks in the prior art to be eliminated. This is achieved by means of the arrangement of the invention, characterized in that the arrangement comprises a discharge space, which is connected to an interspace formed between the anesthetic bottle and the valve device located in the filling device when the anesthetic bottle is being pulled outward, and a closing member, which, as a result of the anesthetic bottle being pulled outward, is arranged to open a flow connection between the interspace and the discharge space before the connection between the anesthetic bottle and the filling device opens.

An advantage of the arrangement of the invention is, above all, that anesthetic and gaseous anesthetic remaining in the interspace can be directed to a desired place in a fully controlled manner, the apparatus thus offering better properties in use than prior art devices. A further advantage of the invention is its simplicity, due to which the invention is advantageous to implement and to use.

Figure 5:
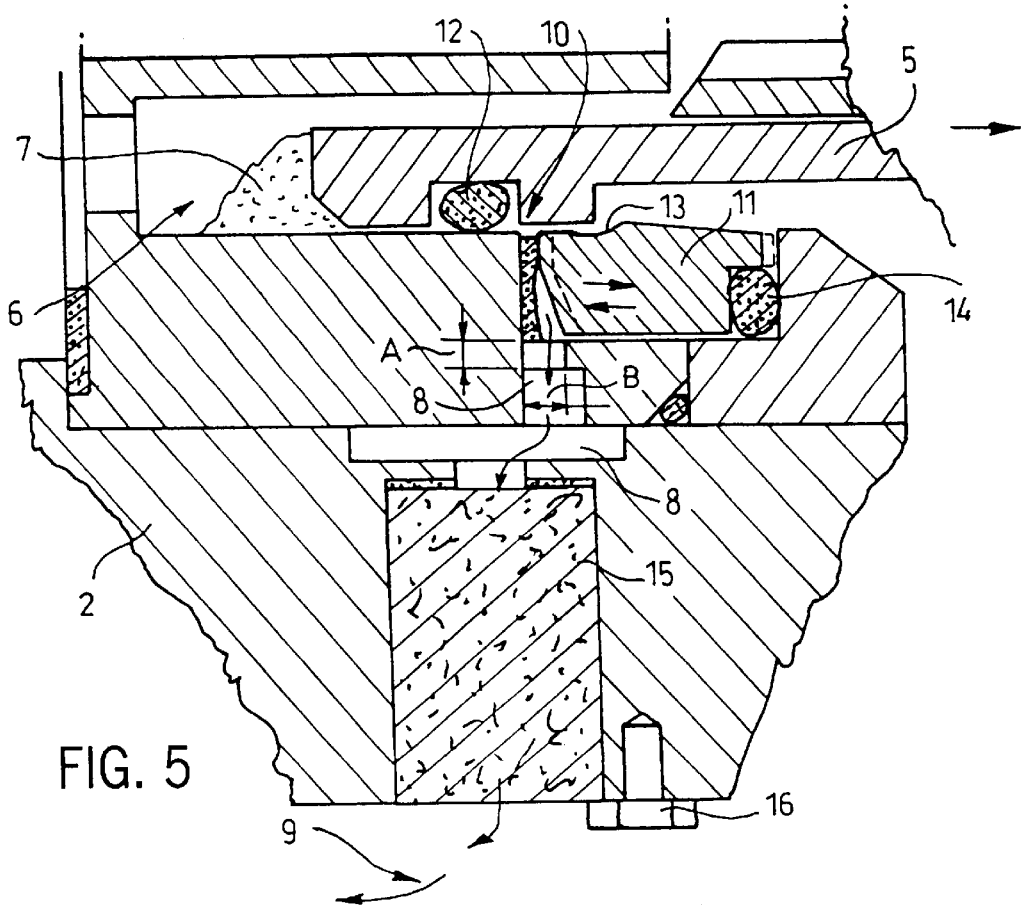
Figure 6:
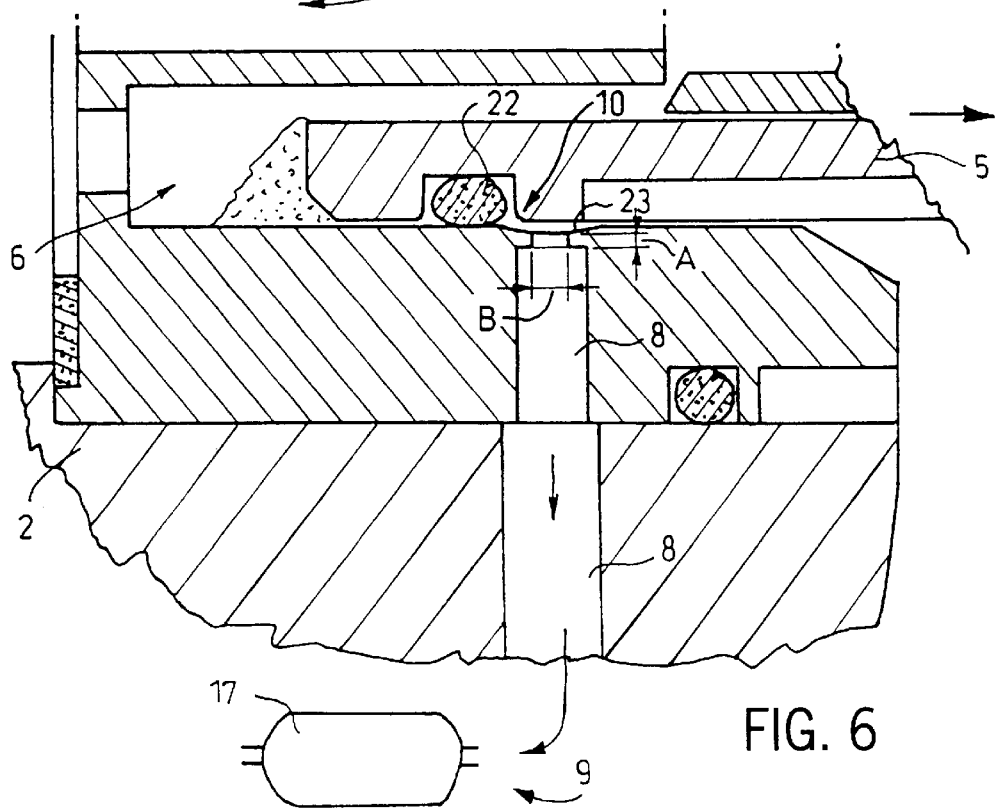

In the following the invention will be described in greater detail with reference to applications shown in the attached drawings, in which FIGS. 1 to 4 illustrate a prior art solution at difference phases of a filling situation;

FIG. 5 is a schematic view illustrating a first embodiment of an arrangement of the invention; and FIG. 6 is a schematic view illustrating a second embodiment of the arrangement of the invention.

FIGS. 1 to 4 illustrate a prior art connection of a desflurane anesthetic vaporizer and an anesthetic bottle at different phases of a normal filling situation. The vaporizer is indicated in FIGS. 1 to 4 with a reference numeral 1, the filling device of the vaporizer with a reference numeral 2 and the anesthetic dispensing cylinder, i.e. the bottle, with a reference numeral 3. A valve device in the filling device 2 is indicated with a reference numeral 4 and a valve device in the bottle 3 with a reference numeral 5. A valve device in the bottle is not required for all anesthetics. When desflurane is used, the bottle must have a valve device because desflurane is vaporized in room temperature. FIGS. 1 to 4 illustrate a solution intended for desflurane, the bottle thus comprising a valve device. The valve device or devices can be arranged to open and close with the impact of the bottle movement, as in the examples shown in the Figures. This is not, however, the only alternative; the opening and closing of the valve devices can also be implemented by means of a separate control, for example.

FIG. 1 illustrates the actual filling phase of a normal filling situation. In this phase the bottle 3 is pushed into the filling device 2, a tight joint being thus formed between the bottle 3 and the filling device 2. The valve devices 4 and 5 are open in this phase, the anesthetic flowing through the open valve devices 4, 5 to the container of the vaporizer 1, as shown with arrows in FIG. 1.

Figure 2:
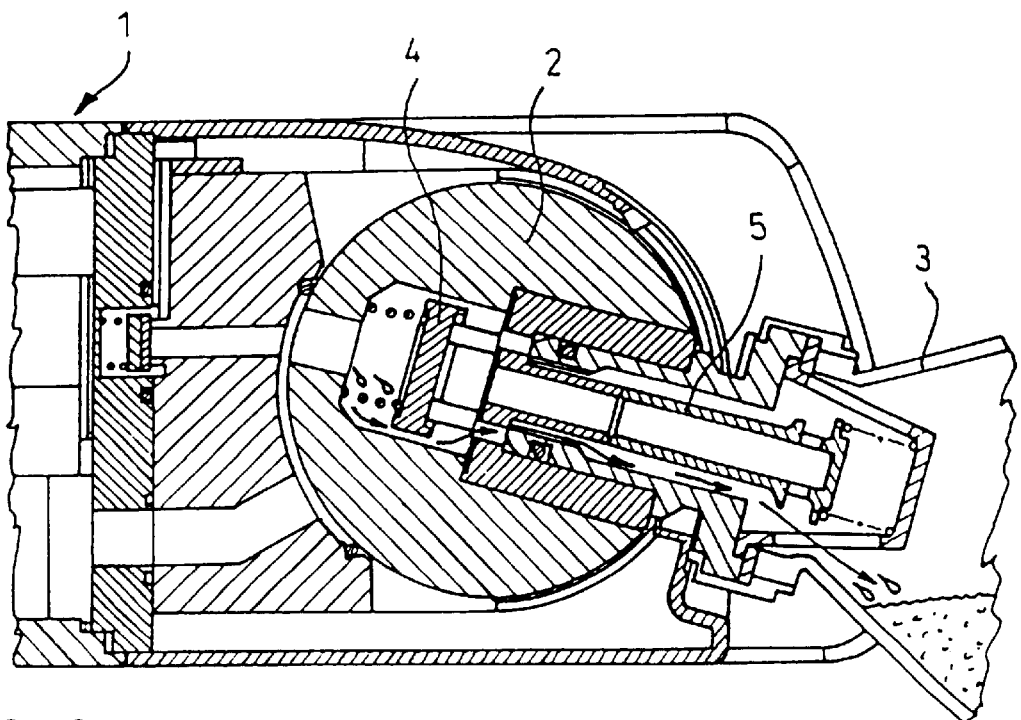

FIG. 2 shows an early stage in the completion of the filling phase where the bottle 3 is turned to a low position. The direction of the turning movement is shown by means of arrows in FIG. 1. In this phase the valve devices 4, 5 are open and the anesthetic in the conduits flows back into the bottle 3 through the open valve devices 4, 5, as shown with arrows in FIG. 2.

Figure 3:
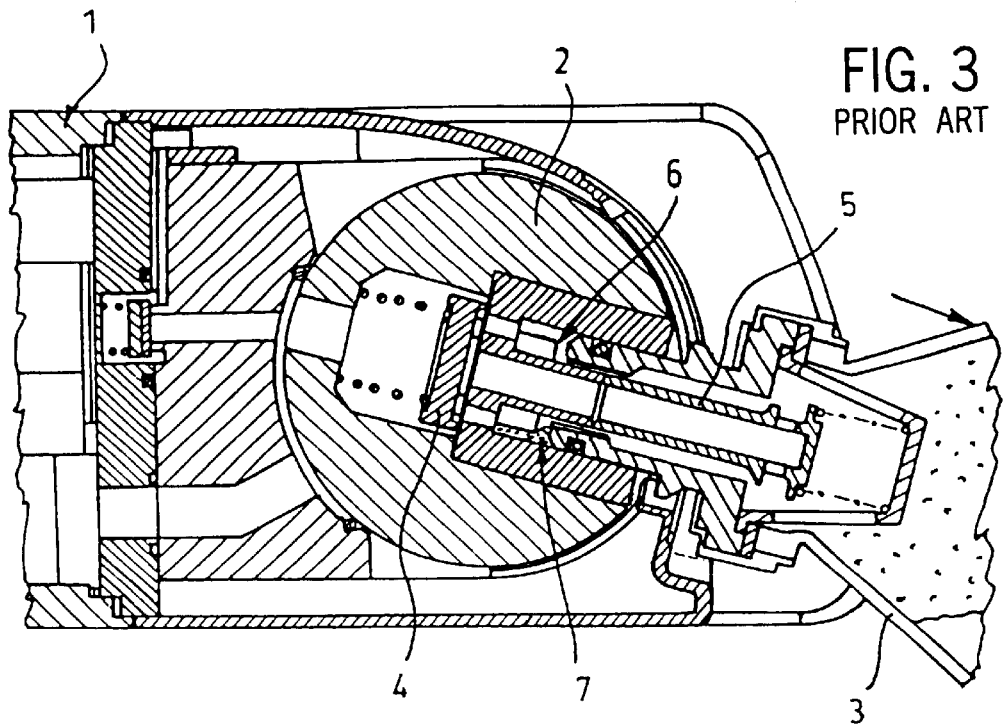

FIG. 3 illustrates a phase following the completion of the filling phase. In this phase the anesthetic bottle 3 is pulled outward as shown with an arrow in FIG. 3. In the situation shown in FIG. 3 the anesthetic bottle 3 is pulled outward such that the valve devices 4, 5 are closed and anesthetic is collected at the bottom of the interspace formed between the valve device 4 and the anesthetic bottle 3. An anesthetic portion 7 collecting in this phase at the bottom of the interspace causes problems, as will be shown later.

Figure 4:
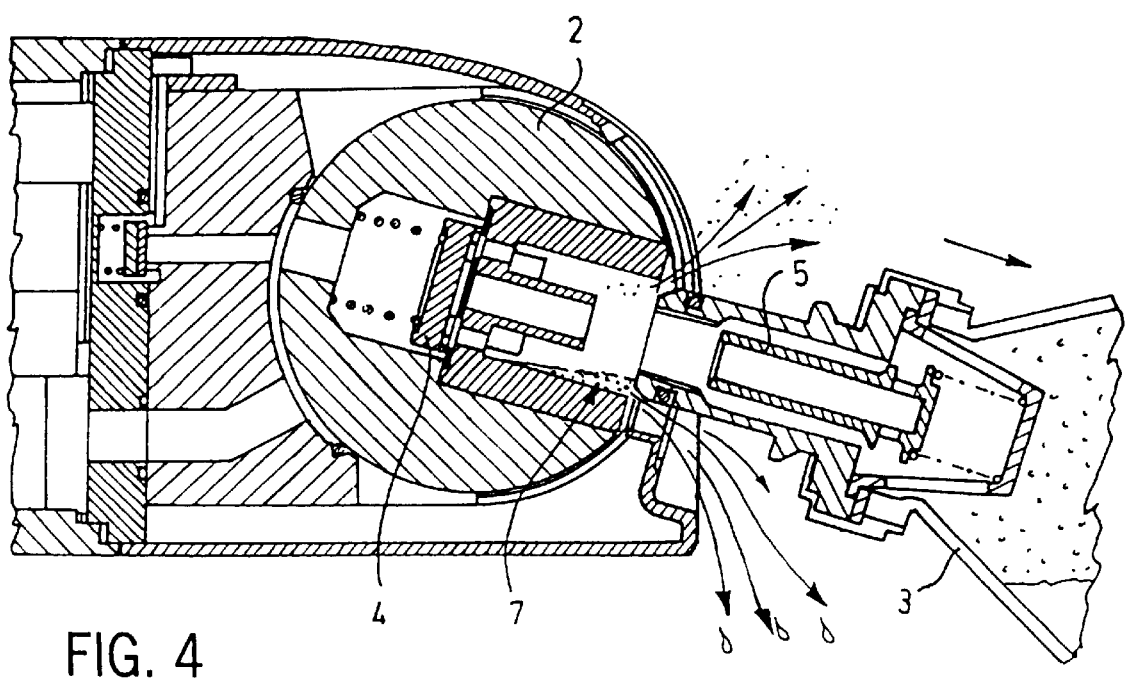

FIG. 4 shows the final stage of the completion of the filling phase. In this stage the anesthetic bottle 3 is pulled further outward such that the sealing surfaces between the bottle 3 and the filling device 2 become detached from one another, the anesthetic portion 7 being released into the environment at a pressure P. The anesthetic is released upwards mostly as a vapour beam and downward as droplets and as a vapour beam, as shown in FIG. 4. FIG. 4 also shows that the operator's fingers may come into contact particularly with the anesthetic dripping downward. This is problematic, because it is known that skin contact with anesthetic agents should be avoided.

FIG. 5 illustrates a first embodiment of the arrangement of the invention. FIG. 5 is a partial enlargement of the solution shown in FIGS. 1 to 4, with details of the invention being added thereto. In FIG. 5, the same reference numeral are used for points corresponding to those in FIGS. 1 to 4. An essential characteristic in the arrangement of the invention is that the arrangement comprises a discharge space 8, 9 connected to an interspace 6 formed between a valve device 4 in the filling device 2 and an anesthetic bottle 3 when the anesthetic bottle 3 is being pulled out, and a closing member 10 which, as a result of the movement of pulling out of the anesthetic bottle 3, has been arranged to open a flow connection between the interspace 6 and the discharge space 8, 9, before the connection between the anesthetic bottle 3 and the filling device 2 opens, so instead of the pressurized gaseous anesthetic that remains in the interspace 6 being released in an uncontrolled manner, it is directed to a desired location in a controlled manner. Interspace refers to a space between the opening of the anesthetic bottle and the filling device surrounding the opening.

In the embodiment shown in FIG. 5, the closing member 10 formed of a moving ring-shaped closing unit 11, which is arranged to move, with the impact of an outward movement of the anesthetic bottle 3 from the filling device 2, from a first position that closes the flow connection to a second position where the flow position is open. The position of the closing unit 11 is shown with dashed lines in FIG. 5. The anesthetic bottle 3 being moved further outward, the closing unit 11 is arranged to move back to the first position with the impact of a spring force or the like. This position of the closing unit 11 is shown with continuous lines in FIG. 5. The movement of the closing unit 11 along with the outward movement of the anesthetic bottle 3 is provided by a ring seal 12 located by the valve of the bottle 3 being arranged to rest on a counter surface 13 formed at the closing unit 11 when the anesthetic bottle 3 is moved outward, thus moving the closing unit from the first position to the second position, i.e. from a 'closed' position to an 'open' position. The ring seal 12 resting on the counter face 13 is arranged to detach when the anesthetic bottle 3 is moved further outward, a seal/spring 14 in the embodiment in FIG. 5 then producing a spring force, the impact of which returns the closing unit 11 from the second position back to the first position which closes the flow connection. The spring force can naturally also be provided by means of a spring means, the sealing being then performed by means of separate seals.

The arrangement according to FIG. 5 operates in principle in the following way. In the final phase of the filling situation the anesthetic bottle 3 is pulled outward (the situation in FIG. 3), whereby the valve members 4, 5 close. As the outward movement continues, an outer seal 12, e.g. an O-ring, of the valve of the bottle 3 extends to the counter surface 13 of the closing unit 11, and the closing unit 11 begins to move, as shown with dashed lines by the upper arrow in FIG. 5, to the second position, i.e. the 'open' position. A flow path to the discharge space 8, 9 then opens for the anesthetic 7 collected into the interspace 6. In the embodiment shown in FIG. 5 the discharge space 8, 9 comprises a conduit part 8 through which the anesthetic collected into the interspace 6 is conducted into an environment 9 of the anesthesia apparatus, the environment being a part of the discharge space. Into the conduit part 8 can also be placed, when needed, a filter unit or filter units 15, for instance activated carbon filters or other similar filters, from which the anesthetic evaporates slower or in a less harmful form into the environment in due course. The locking of the filter units 15 is schematically shown in FIG. 5 with a reference numeral 16. The space to which the anesthetic is released can be the surroundings of the anesthesia apparatus, such as a suitable spatter-proof space. The space can also be a closed container where the anesthetic released through the conduit part 8 is cooled, its pressure decreasing at the same time. The container can naturally also be a cooled container, in which case the flow proceeds freely. The anesthetic released from the interspace can naturally also be conducted back into the vaporizer container by periodically opening a conduit for example between the filter unit and the vaporizer container or, correspondingly, between the above mentioned container and the vaporizer container. The connection can be provided by means of conduits and suitable valves. The discharge space 8, 9 can also be formed of the conduit part 8 by creating the conduit part as a recess or a niche where the released anesthetic is conducted. The capacity of the recess has to be dimensioned sufficiently large to allow the pressure to reduce to an acceptable level. The recess can naturally also be connected to the vaporizer container, similarly as described above in connection with the closed container. The discharge space, such as the conduit part, can also be provided with suction or underpressure to enhance the releasing of the anesthetic. Suction or underpressure can be provided for example by means of the hospital exhaust air channel, by connecting the conduit part to the hospital exhaust air channel, for example.

As the outward movement of the anesthetic bottle 3 continues, the seal 12 is detached from the counter surface 13 of the closing unit 11, the closing unit 11 then moving, as shown by the lower arrow in FIG. 5, back to the first position closing the flow path, which in this embodiment is the conduit part 8. The force generating the movement of the closing unit is supplied by the flexible ring seal 14 which is compressed when the closing unit 11 moves to right, in the case shown in FIG. 5, along with the anesthetic bottle 3. As the seal 12 detaches from the counter surface 13, the seal ring 14 regains its original form, moving at the same time the closing unit 11 back to its first position, thus closing the conduit part 8.

To the releasing of the overpressurized interspace 6 it is advantageous that the dimensions A and B of the opening from the interspace 6 to the discharge space 8, 9 are formed such that the flow is throttled so as to make most of the anesthetic liquid that is released from the interspace leave the interspace pushed by the pressure. The dimensions A and B can be of the order of A=1 mm and B=0.6 mm, for example.

FIG. 6 schematically illustrates a second embodiment of the invention. The embodiment in FIG. 6 differs from the one in FIG. 5 in the method of forming of the closing member 10. In other respects the example shown in FIG. 6 substantially corresponds to the one shown in FIG. 5. In FIG. 6, the same reference numerals are used for points corresponding to those in FIG. 5. In the application shown in FIG. 6 the closing member 10 is formed in the area of the ring seal 22, located by the valve of the anesthetic bottle 3, and the opening leading to the discharge space 8, 9; the closing member being formed of a surface 23 that fits the ring seal 22 formed at the tip of the conduit part 8.

The embodiment in FIG. 6 operates in principle as follows. At the end of the filling situation, the anesthetic bottle 3 is pulled outward from the filling device 2, the valve devices 4 and 5 closing at the same time. As the outward movement of the anesthetic bottle 3 from the filling device 2 continues further, the ring seal 22 located by the valve device 5 reaches the opening integrated to the filling part 2 and leading to the discharge space 8, 9, the ring seal 22 gliding over the opening as the movement continues. The co-operation between the seal ring and the surface 23 that fits the seal ring 22 then opens the flow path from the interspace 6 to the discharge space 8, 9 and the anesthetic collected in the interspace is released to a desired space. The discharge space 8, 9 can be any one of the alternatives given in connection with FIG. 5. In connection with FIG. 6, an alternative is schematically illustrated in which the discharge space 8, 9 comprises a closed container 17, which can also be cooled, as described above in connection with FIG. 5. The anesthetic can be conducted from the container 17 back to the vaporizer container as described above. Also in connection with this embodiment, the opening leading from the interspace 6 to the discharge space 8, 9 is advantageously formed as an opening throttling the flow. The opening is described in FIG. 6 by using dimensions A and B, similarly as in FIG. 5. The above examples of the embodiments of the invention are in no way meant to restrict the invention, but the invention can be freely modified within the scope of the claims. It is therefore obvious that an arrangement of the invention or its details do not necessarily need to be exactly like the ones shown in the drawings, but other solutions are also possible. The closing member, for example, can be formed of an electrically controlled valve member in such a way that a control signal is provided to the valve member by the movement of the anesthetic bottle, etc.

What is claimed is:

1. An anesthetic apparatus comprising:
   a filling device for an anesthetic vaporizer, said filling device having a first port and having a second, discharge port formed therein;
   an anesthetic bottle insertable in said first port of said filling device to supply anesthetic to the vaporizer, an interspace containing anesthetic being formed in said filling device during withdrawal of the anesthetic bottle from said first port of said filling device; and
   a closing member operatively associated with said second, discharge port in said filling device, said closing member having a first condition blocking fluid communication between the interspace and said discharge port, said closing member being placed in a second condition responsive to the removal of the anesthetic bottle from said first port of said filling device in which the discharge port is placed in fluid communication with the interspace to remove anesthetic from the interspace through the discharge port prior to separation of the anesthetic bottle from said first port of said filling device at the end of the withdrawal.

2. An arrangement according to claim 1, wherein said second, discharge port comprises a conduit.

3. An arrangement according to claim 2, wherein the conduit is provided with a filter unit.

4. An arrangement according to claim 2, wherein the conduit is arranged to provide a connection to the ambient surroundings of the anesthesia apparatus.

5. An arrangement according to claim 2, wherein the conduit is arranged to provide a connection to a spatter-proof space.

6. An arrangement according to claim 2, wherein the conduit is arranged to provide a connection to a closed container.

7. An arrangement according to claim 2 wherein said conduit is arranged to form a discharge space for the anesthetic from the interspace.

8. An arrangement according to claim 1 wherein said second discharge port is formed as an opening throttling the flow of anesthetic from the interspace.

9. An arrangement according to claim 1 wherein said closing member is formed as a movable closing unit, and wherein said anesthetic bottle carries means is engageable with said closing unit in the course of withdrawing the anesthetic bottle from said first port of said filling device, to move said closing unit from a first position blocking fluid communication between the interspace and said first port to a second position in which said first port is placed in fluid communication with the interspace, said closing unit having means for returning said closing unit to the first position when engagement of said closing unit with the means carried by the anesthetic bottle is concluded.

10. An arrangement according to claim 9 wherein the anesthetic bottle has a ring seal and wherein said movable closing unit has a counter surface which engages the ring seal as the anesthetic bottle is withdrawn from said first port of said filling device and thereafter disengages the ring seal to allow said returning means to return said closing unit to the first position.

11. An arrangement according to claim 9 wherein said closing unit has a resilient member for returning said closing unit to the first position when engagement of said closing unit with the means carried by the aesthetic bottle is concluded.

12. An arrangement according to claim 11 wherein said resilient member further comprises a seal member for sealing said closing unit with respect to said filling device.

13. An arrangement according to claim 9 wherein said closing unit has a seal member for sealing said closing unit with respect to said filling device.

14. An arrangement according to claim 1 wherein said closing member is formed as a ring seal carried by the anesthetic bottle, said ring seal engaging an inner surface of the filling device to block fluid communication between the interspace and said second, discharge port, said second discharge port having a recessed opening in the inner surface of the filling device that removes the engagement of the ring seal with the inner surface of the filling device to provide fluid communication between the interspace and said second, discharge port as the anesthetic bottle is withdrawn from said first port of said filling device.

* * * * *